United States Patent
Lin et al.

(10) Patent No.: US 6,840,995 B2
(45) Date of Patent: Jan. 11, 2005

(54) PROCESS FOR PRODUCING FAST-SETTING, BIORESORBABLE CALCIUM PHOSPHATE CEMENTS

(75) Inventors: Jiin-Huey Chern Lin, Winnetka, IL (US); Chien-Ping Ju, Carbondale, IL (US); Kuan-Liang Lin, Tainan (TW); I-Chang Wang, Tainan (TW)

(73) Assignee: Calcitec, Inc., Saratoga, CA (US)

( * ) Notice: Subject to any disclaimer, the term of this patent is extended or adjusted under 35 U.S.C. 154(b) by 46 days.

(21) Appl. No.: 10/328,019

(22) Filed: Dec. 26, 2002

(65) Prior Publication Data

US 2003/0121450 A1 Jul. 3, 2003

Related U.S. Application Data

(63) Continuation-in-part of application No. 09/615,384, filed on Jul. 13, 2000, now abandoned, which is a continuation-in-part of application No. 09/351,912, filed on Jul. 14, 1999, now Pat. No. 6,379,453.

(51) Int. Cl.$^7$ .............................................. C04B 12/02
(52) U.S. Cl. ........................... 106/690; 106/35; 106/691
(58) Field of Search ........................... 106/35, 690, 691

(56) References Cited

U.S. PATENT DOCUMENTS 6,379,453 B1 * 4/2002 Lin et al. ..................... 106/690

* cited by examiner

Primary Examiner—C. Melissa Koslow
(74) Attorney, Agent, or Firm—Gray Cary Ware & Freidenrich, LLP

(57) ABSTRACT

A fast-setting, bioresorbable calcium phosphate cement is prepared by a process which can be carried out with a heat treatment up to 1000° C. on a mixture of a wetting solution and a calcium phosphate powder having a Ca to P molar ratio of 0.5–2.5. The wetting solution suitable for use in the process of the present invention includes water, an organic solvent, an acidic and basic solution. A setting solution for mixing with the heated powder to form the fast-setting, bioresorbable calcium phosphate cement may be water, an acidic or basic solution according to the process of the present invention.

14 Claims, No Drawings

PROCESS FOR PRODUCING FAST-SETTING, BIORESORBABLE CALCIUM PHOSPHATE CEMENTS

CROSS-REFERENCE TO RELATED APPLICATION

The present application is a continuation-in-part application of U.S. patent application Ser. No. 09/615,384, filed Jul. 13, 2000, now abandoned, which is a continuation-in-part application of U.S. patent application Ser. No. 09/351,912, filed Jul. 14, 1999, now U.S. Pat. No. 6,379,453B1. The above-listed applications are commonly assigned with the present invention and the entire contents of which are incorporated herein by reference.

FIELD OF THE INVENTION

The present invention relates to a process for producing fast-setting, bioresorbable calcium phosphate cements (CPC), and in particular, to a process including a pre-heat treatment step to generate whiskers or fine crystals on surfaces of the CPC particles.

DESCRIPTION OF THE RELATED ART

U.S. Pat. No. 6,379,453B1 which is commonly assigned with the present invention discloses a process for producing a fast-setting, bioresorbable calcium phosphate cement comprising the following steps: obtaining a powder mixture from at least one calcium phosphate selected from the group consisting of $Ca_4(PO_4)_2O$, $CaHPO_4.2H_2O$, $CaHPO_4$, $Ca_8H_2(PO_4)_6.5H_2O$, alpha-$Ca_3(PO_4)_2$, beta-$Ca_3(PO_4)_2$, $Ca_2P_2O_7$, $Ca_2H_2P_2O_8$, wherein the molar ratio of Ca to P in the mixture is roughly between 1 and 2; mixing the powder mixture in a phosphate-containing solution to obtain a powder/solution mixture having a concentration of less than 4 g powder mixture per ml solution; immediately heating the powder/solution mixture to a temperature of roughly 50° C.–350° C. to obtain a powder containing uniformly distributed submicron-sized apatite crystals; and mixing the apatite crystal-containing powder in a phosphate ion-containing solution to obtain a fast-setting, bioresorbable calcium phosphate cement.

SUMMARY OF THE INVENTION

An extensive study on the preparation of the fast-setting, bioresorbable calcium phosphate cement disclosed in U.S. Pat. No. 6,379,453B1 has been conducted by the same inventors and their co-workers, and found that the fast-setting, bioresorbable calcium phosphate cement can be prepared under various conditions. Therefore an object of the invention is to provide a more comprehensive process for producing a fast-setting, bioresorbable calcium phosphate cement.

The invention accomplishes the above object by providing a process which can be carried out with a heat treatment up to 1000° C. on a mixture of a wetting solution and a calcium phosphate powder having a Ca to P molar ratio of 0.5–2.5. The wetting solution suitable for use in the process of the present invention includes water, an organic solvent, an acidic and basic solution, not limited to the phosphate-containing solution. A setting solution for mixing with the heated powder to form the fast-setting, bioresorbable calcium phosphate cement may be an acidic solution, a basic solution or substantially pure water according to the process of the present invention.

DETAILED DESCRIPTION OF THE INVENTION

The preferred embodiments of the present invention include (but not limited to) the following:

A process for producing a fast-setting, bioresorbable calcium phosphate cement, comprising the following steps:

(a) obtaining a calcium phosphate powder comprising at least one calcium phosphate selected from the group consisting of $Ca_4(PO_4)_2O$, $CaHPO_4.2H_2O$, $CaHPO_4$, $Ca_8H_2(PO_4)_6.5H_2O$, alpha-$Ca_3(PO_4)_2$, beta-$Ca_3(PO_4)_2$, $Ca_2P_2O_7$, $Ca_2H_2P_2O_8$, wherein the molar ratio of Ca to P in said calcium phosphate powder is between about 0.5 and 2.5;

(b) mixing said calcium phosphate powder obtained from step (a) with a wetting solution to obtain a powder/solution mixture in a ratio of less than about 10 g powder per ml solution;

(c) heating the powder/solution mixture resulting from step (b) to a temperature greater than room temperature up to about 1000° C.; and (d) mixing the resulting dried powder from step (c) in a setting solution to obtain the fast-setting, bioresorbable calcium phosphate cement.

2) The process as set forth in item 1), wherein said Ca/P molar ratio in step (a) is between 1.0 and 2.0.

3) The process as set forth in item 2), wherein in step (d) the resulting dried powder from step (c) together with at least one additive selected from the group of sodium phosphate ($Na_3PO_4$), disodium hydrogen phosphate ($Na_2HPO_4$), sodium dihydrogen phosphate ($NaH_2PO_4$), disodium hydrogen phosphate dodecahydrate ($Na_2HPO_4.12H_2O$), disodium hydrogen phosphate heptahydrate ($Na_2HPO_4.7H_2O$), sodium phosphate dodecahydrate ($Na_3PO_4.12H_2O$), orthophosphoric acid ($H_3PO_4$), calcium sulfate ($CaSO_4$), $Ca_4(PO_4)_2O$, $CaHPO_4.2H_2O$, $CaHPO_4$, $Ca_8H_2(PO_4)_6.5H_2O$, alpha-$Ca_3(PO_4)_2$, beta-$Ca_3(PO_4)_2$, $Ca_2P_2O_7$, and $Ca_2H_2P_2O_8$, are mixed with the setting solution to obtain the fast-setting, bioresorbable calcium phosphate cement.

4) The process as set forth in item 3), wherein said wetting solution in step (b) is an acidic aqueous solution, a basic aqueous solution, an organic solvent, or substantially pure water.

5) The process as set forth in item 4), wherein the organic solvent is ethanol.

6) The process as set forth in item 1), wherein the mixing ratio in step (b) is less than about 5 g powder per ml solution.

7) The process as set forth in item 1), wherein the heating temperature in step (c) is greater than room temperature up to about 500° C.

8) The process as set forth in item 1), wherein the setting solution in step (d) is an acidic aqueous solution, a basic aqueous solution, or a substantially pure water.

9) The process as set forth in item 4) or 8), wherein the acidic aqueous solution is selected from the group consisting of nitric acid ($HNO_3$), hydrochloric acid (HCl), phosphoric acid ($H_3PO_4$), carbonic acid ($H_2CO_3$), sodium dihydrogen phosphate ($NaH_2PO_4$), sodium dihydrogen phosphate monohydrate, sodium dihydrogen phosphate dihydrate, potassium dihydrogen phosphate ($KH_2PO_4$), ammonium dihydrogen.phosphate ($NH_4H_2PO_4$), malic acid, acetic acid, lactic acid, citric acid, malonic acid, succinic acid, glutaric acid, tartaric acid, oxalic acid and their mixture.

10) The process as set forth in item 4) or 8), wherein the basic aqueous solution is selected from the group consisting of ammonia, ammonium hydroxide, alkali metal hydroxide, alkaline earth hydroxide, disodium hydrogen phosphate ($Na_2HPO_4$), disodium hydrogen phosphate dodecahydrate, disodium hydrogen phosphate heptahydrate, sodium phosphate dodecahydrate ($Na_3PO_4.12H_2O$), dipotassium hydrogen phosphate ($K_2HPO_4$), potassium phosphate tribasic ($K_3PO_4$), diammonium hydrogen phosphate (($NH_4)_2HPO_4$, ammonium phosphate trihydrate ($(NH_4)_3PO_4 \cdot 3H_2O$), sodium bicarbonate ($NaHCO_3$), and their mixture.

11) The process as set forth in item 1) further comprising grinding the resulting dried powder from step (c) between step (c) and step (d).

12) The process as set forth in item 1), wherein the fast-setting, bioresorbable calcium phosphate cement obtained from step (d) has a viscosity so that it can be injected by a syringe.

The following examples are intended to demonstrate the invention more fully without acting as a limitation upon its scope, since numerous modifications and variations will be apparent to those skilled in this art.

EXAMPLE 1

To fabricate the CPC, the TTCP ($Ca_4(PO_4)_2O$) powder was prepared from the reaction of dicalcium pyrophosphate ($Ca_2P_2O_7$) (Sigma Chem. Co., St Louis, Mo., USA) and calcium carbonate ($CaCO_3$) (Katayama Chem. Co., Tokyo, Japan) using the method suggested by Brown and Epstein [*Journal of Research of the National Bureau of Standards—A Physics and Chemistry* 6 (1965) 69A 12], while the DCPA ($CaHPO_4$) powder is a commercial product (Jassen Chemical Co., Japan).

5 g of a mixed powder of DCPA and TTCP in 1:1 molar ratio and 1.6 ml of a wetting solution of a phosphoric acid aqueous solution having a pH of 1.96 were mixed, and stirred for one minute. The resulting mixture was placed into an oven at 50° C. for 15 minutes, and the resulting dried mixture was mechanically ground for 20 minutes to fine particles after being removed from the oven. 1 g of the fine particles and 0.4 ml of phosphate aqueous solution (1.0 M, pH=6.0) were mixed to form a paste, which was tested every 30 seconds to determine the working time and the setting time. The setting time is the time required when a 1 mm diameter pin with a load of ¼ pounds can be inserted only 1 mm deep into the surface of the paste. The working time is the time after which the paste is too viscous to be stirred. The working time of the paste of this example is 6.5 minutes and the setting time thereof is 11.5 minutes.

The paste was placed in a relatively large amount of deionized water immediately following the formation thereof, and it was observed that the paste was non-dispersive in deionized water.

EXAMPLES 2–5

The procedures of Example 1 were repeated except that the heat treatment at 50° C. for 15 minutes was changed according to the conditions listed in Table 1. The performance is also listed in Table 1.

TABLE 1

|  | Controlling treatment | Setting/working time (min) | Dispersive in water |
| --- | --- | --- | --- |
| Ex. 1 | Heating, 50° C. | 11.5/6.5 | No |
| Ex. 2 | Heating, 100° C. | 13.5/8.0 | No |
| Ex. 3 | Heating, 150° C. | 8.5/8.0 | No |
| Ex. 4 | Heating, 500° C. | 2.5/1.5 | No |
| Ex. 5 | Heating, 1000° C. | 35/31 | No |

EXAMPLES 6–10

The procedures of Example 1 were repeated by using the calcium phosphate powders and the wetting solutions listed in Table 2. The performance is also listed in Table 2.

TABLE 2

|  | Calcium phosphate powder* | Wetting solution | Setting/working time (min) | Dispersive in water |
| --- | --- | --- | --- | --- |
| Ex. 6 | TCP | Phosphoric acid | 10/6.5 | No |
| Ex. 7 | TCP | Ethanol | 12.5/8.5 | No |
| Ex. 8 | TTCP + DCPA | Phosphoric acid | 11/8 | No |
| Ex. 9 | TTCP + DCPA + TCP | Phosphoric acid | — | No |
| Ex. 10 | DCPA + TCP | Phosphoric acid | 29/24 | No |

*TCP is anhydrous tricalcium phosphate. TTCP + DCPA is a mixed powder of TTCP and DCPA in 1:1 molar ratio. TTCP + DCPA + TCP is a mixed powder of TTCP + DCPA and TCP in 1:1 weight ratio. DCPA + TCP is a mixed powder of DCPA and TCP in 1:2 molar ratio.

EXAMPLES 11–22

The procedures of Example 1 were repeated by using the wetting solutions having different pH values listed in Table 3. The performance is also listed in Table 3.

TABLE 3

|  | Wetting solution | pH | Dispersive in water |
| --- | --- | --- | --- |
| Ex. 11 | Phosphoric acid | 0.56 | No |
| Ex. 12 | Phosphoric acid | 1.03 | No |
| Ex. 13 | Phosphoric acid | 1.17 | No |
| Ex. 14 | Phosphoric acid | 1.22 | No |
| Ex. 15 | Phosphoric acid | 1.32 | No |
| Ex. 16 | Phosphoric acid | 2.0 | No |
| Ex. 17 | Acetic acid + sodium carbonate | 7.0 | No |
| Ex. 18 | Sodium hydroxide | 9.5 | No |
| Ex. 19 | Sodium hydroxide | 12.55 | No |
| Ex. 20 | Acetic acid | 1.96 | No |
| Ex. 21 | Ethanol | — | No |
| Ex. 22 | Deionized water | 7.0 | No |

In the following examples, different setting solutions were used to verify the effect of the setting solution on the non-dispersive property of the calcium phosphate cement.

EXAMPLES 23–30

5 g of a mixed powder of DCPA and TTCP in 1:1 molar ratio and 1.6 ml of a wetting solution of 25 mM phosphoric acid aqueous solution were mixed, and stirred for one minute. The resulting mixture was placed into an oven at 50° C. for 15 minutes, and the resulting dried mixture was mechanically ground for 20 minutes to fine particles after being removed from the oven. 1 g of the fine particles and 0.4 ml of the setting solutions listed in Table 4 were mixed to form a paste, which was tested every 30 seconds to determine the working time and the setting time as defined in Example 1. The results are shown in Table 4.

EXAMPLES 31–33

The procedures of Example 23 were repeated except that an additive as shown in Table 4 was added to the mixed powder of DCPA and TTCP in a weight ratio of 1:10 after the mixed powder was removed from the oven, and the setting solution used in these examples was deionized water. The results are shown in Table 4.

EXAMPLES 34–45

To 5 g TTCP powder which was used as synthesized 10 ml of 1M phosphoric acid aqueous solution was poured, and the mixture was filtered immediately. The filtered cake was placed into an oven at 150° C. for 10 minutes, and the resulting dried mixture was mechanically ground for 5 hours to fine particles. The resulting heat treated TTCP fine particles and the TTCP powder as synthesized (without heat treatment) were mixed in a weight ratio of 1:1. 1 g of the mixed TTCP powder and 0.4 ml of the setting solutions listed in Table 4 were mixed to form a paste, which was tested every 30 seconds to determine the working time and the setting time as defined in Example 1. The results are shown in Table 4.

TABLE 4

| | Powder | Setting solution | pH | Dispersive in water | Setting/ working time (min) |
|---|---|---|---|---|---|
| Ex. 23 | TTCP + DCPA | 25 mM $H_3PO_4$ | 1.96 | No | |
| Ex. 24 | TTCP + DCPA | Acetic acid | — | No | |
| Ex. 25 | TTCP + DCPA | $HNO_3$ | — | No | |
| Ex. 26 | TTCP + DCPA | HCl | — | No | |
| Ex. 27 | TTCP + DCPA | $(NH_4)_2HPO_4$ | 7.96 | No | 13.0/8.0 |
| Ex. 28 | TTCP + DCPA | $K_2HPO_4$ | 8.76 | No | 31.0/23.5 |
| Ex. 29 | TTCP + DCPA | NaOH | 13.57 | No | 28.0/19.0 |
| Ex. 30 | TTCP + DCPA | Deionized water | 7.0 | No | |
| Ex. 31 | TTCP + DCPA + phosphoric acid | Deionized water | 7.0 | No | |
| Ex. 32 | TTCP + DCPA + $NaH_2PO_4.2H_2O$ | Deionized water | 7.0 | No | 20.5/16.5 |
| Ex. 33 | TTCP + DCPA + $Na_2HPO_4.12H_2O$ | Deionized water | 7.0 | No | 11.0/7.0 |
| Ex. 34 | TTCP | Deionized water | 7.0 | No | 35.0/31.0 |
| Ex. 35 | TTCP | 3M $H_3PO_4$ | −0.7 | No | 17.5/16.0 |
| Ex. 36 | TTCP | HCl | −1.53 | No | |
| Ex. 37 | TTCP | HCl | −0.83 | No | 22.5/17.5 |
| Ex. 38 | TTCP | $HNO_3$ | −1.53 | No | |
| Ex. 39 | TTCP | $HNO_3$ | −0.83 | No | 33/28.5 |
| Ex. 40 | TTCP | $HNO_3$ | 0 | No | 27.5/22.0 |
| Ex. 41 | TTCP | $HNO_3$ | 2 | No | 20.5/16.0 |
| Ex. 42 | TTCP | $K_2HPO_4$ | 8.76 | No | 9.0/7.5 |
| Ex. 43 | TTCP | $(NH_4)_2HPO_4$ | 7.96 | No | 8.5/6.5 |
| Ex. 44 | TTCP | $CH_3COOH$ | | No | 4.5/3.5 |
| Ex. 45 | TTCP | NaOH | 13.57 | No | 52/30 |

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A process for producing a fast-setting, bioresorbable calcium phosphate cement, comprising the following steps:
   (a) obtaining a calcium phosphate powder comprising at least one calcium phosphate selected from the group consisting of $Ca_4(PO_4)_2O$, $CaHPO_4.2H_2O$, $CaHPO_4$, $Ca_8H_2(PO_4)_6.5H_2O$, alpha-$Ca_3(PO_4)_2$, beta-$Ca_3(PO_4)_2$, $Ca_2P_2O_7$, $Ca_2H_2P_2O_8$, wherein the molar ratio of Ca to P in said calcium phosphate powder is between about 0.5 and 2.5;
   (b) mixing said calcium phosphate powder obtained from step (a) with a wetting solution to obtain a powder/solution mixture in a ratio of less than about 10 g powder per ml solution;
   (c) heating the powder/solution mixture resulting from step (b) to a temperature greater than room temperature up to about 1000° C.; and
   (d) mixing the resulting dried powder from step (c) in a setting solution to obtain the fast-setting, bioresorbable calcium phosphate cement.

2. The process as set forth in claim 1, wherein said Ca/P molar ratio in step (a) is between 1.0 and 2.0.

3. The process as set forth in claim 1, wherein in step (d) the resulting dried powder from step (c) together with at least one additive selected from the group of $Na_3PO_4$, $Na_2HPO_4$, $NaH_2PO_4$, $Na_2HPO_4.12H_2O$, $Na_2HPO_4.7H_2O$, $Na_3PO_4.12H_2O$, $H_3PO_4$, $CaSO_4$, $Ca_4(PO_4)_2O$, $CaHPO_4.2H_2O$, $CaHPO_4$, $Ca_8H_2(PO_4)_6.5H_2O$, alpha-$Ca_3(PO_4)_2$, beta-$Ca_3(PO_4)_2$, $Ca_2P_2O_7$, and $Ca_2H_2P_2O_8$, are mixed with the setting solution to obtain the fast-setting, bioresorbable calcium phosphate cement.

4. The process as set forth in claim 1, wherein said wetting solution in step (b) is an acidic aqueous solution, a basic aqueous solution, an organic solvent, or substantially pure water.

5. The process as set forth in claim 4, wherein the acidic aqueous solution is selected from the group consisting of nitric acid, hydrochloric acid, phosphoric acid, carbonic acid, sodium dihydrogen phosphate, sodium dihydrogen phosphate monohydrate, sodium dihydrogen phosphate dihydrate, potassium dihydrogen phosphate, ammonium dihydrogen.phosphate, malic acid, acetic acid, lactic acid, citric acid, malonic acid, succinic acid, glutaric acid, tartaric acid, oxalic acid and their mixture.

6. The process as set forth in claim 4, wherein the basic aqueous solution is selected from the group consisting of ammonia, ammonium hydroxide, alkali metal hydroxide, alkaline earth hydroxide, disodium hydrogen phosphate, disodium hydrogen phosphate dodecahydrate, disodium hydrogen phosphate heptahydrate, sodium phosphate dodecahydrate, dipotassium hydrogen phosphate, potassium phosphate tribasic, diammonium hydrogen phosphate, ammonium phosphate trihydrate, sodium bicarbonate, and their mixture.

7. The process as set forth in claim 4, wherein the organic solvent is ethanol.

8. The process as set forth in claim 1, wherein the mixing ratio in step (b) is less than about 5 g powder per ml solution.

9. The process as set forth in claim 1, wherein the heating temperature in step (c) is greater than room temperature up to about 500° C.

10. The process as set forth in claim 1, wherein the setting solution in step (d) is an acidic aqueous solution, a basic aqueous solution, or a substantially pure water.

11. The process as set forth in claim 10, wherein the acidic aqueous solution is selected from the group consisting of nitric acid, hydrochloric acid, phosphoric acid, carbonic acid, sodium dihydrogen phosphate, sodium dihydrogen phosphate monohydrate, sodium dihydrogen phosphate dihydrate, potassium dihydrogen phosphate, ammonium dihydrogen.phosphate, malic acid, acetic acid, lactic acid, citric acid, malonic acid, succinic acid, glutaric acid, tartaric acid, oxalic acid and their mixture.

12. The process as set forth in claim 10, wherein the basic aqueous solution is selected from the group consisting of ammonia, ammonium hydroxide, alkali metal hydroxide, alkaline earth hydroxide, disodium hydrogen phosphate, disodium hydrogen phosphate dodecahydrate, disodium hydrogen phosphate heptahydrate, sodium phosphate dodecahydrate, dipotassium hydrogen phosphate, potassium phosphate tribasic, diammonium hydrogen phosphate, ammonium phosphate trihydrate, sodium bicarbonate, and their mixture.

13. The process as set forth in claim 1 further comprising grinding the resulting dried powder from step (c) between step (c) and step (d).

14. The process as set forth in claim 1, wherein the fast-setting, bioresorbable calcium phosphate cement obtained from step (d) has a viscosity so that it can be injected by a syringe.

* * * * *